United States Patent [19]

Smith et al.

[11] 4,232,175

[45] Nov. 4, 1980

[54] NITROSATION OF AROMATIC COMPOUNDS

[75] Inventors: William E. Smith; Thomas W. McGee, both of Midland, Mich.

[73] Assignee: The Dow Chemical Company, Midland, Mich.

[21] Appl. No.: 858,508

[22] Filed: Dec. 8, 1977

[51] Int. Cl.³ ............................................. C07C 79/24
[52] U.S. Cl. .................................... 568/706; 423/400
[58] Field of Search ........................ 568/706; 260/647; 423/400

[56] References Cited

U.S. PATENT DOCUMENTS

| | | | |
|---|---|---|---|
| 2,225,358 | 12/1940 | Teter | 568/706 |
| 3,320,324 | 5/1967 | Kavka | 568/706 |
| 3,510,527 | 5/1970 | Prosser | 568/706 |
| 3,517,075 | 6/1970 | Callister | 568/706 |
| 3,519,693 | 7/1970 | Harvey | 568/706 |
| 3,714,267 | 1/1973 | Baldwin | 568/706 |
| 3,770,834 | 11/1973 | Prosser | 568/706 |
| 3,917,719 | 11/1975 | Baldwin | 568/706 |

*Primary Examiner*—Werren B. Lone
*Attorney, Agent, or Firm*—Michael L. Glenn

[57] ABSTRACT

Aromatic compounds in an acidic, aqueous solution can be economically nitrosated by treatment with the hydration products of oxides of nitrogen at a temperature in the range of −15° C. to 10° C. The oxides of nitrogen are generated as a gas from a separate solution or slurry by the reaction of an alkali metal nitrate with a strong mineral acid at a temperature in the range of 15° C. to 35° C. This method of nitrosation employs relatively inexpensive reagents, but can be carried on continuously and produces unexpectedly high yield of para-nitrosated product from a monosubstituted starting material.

14 Claims, No Drawings

NITROSATION OF AROMATIC COMPOUNDS

BACKGROUND OF THE INVENTION

This invention concerns a method of preparing a solution effective in nitrosating nitrosatable aromatic compounds in an acidic, aqueous solution by means of the condensed gaseous reaction products of an alkali metal nitrite and a strong mineral acid.

It is known that sodium nitrite can be reacted with a strong acid in an aqueous solution to produce a solution effective in nitrosating aromatic compounds present in the solution. See, for example, U.S. Pat. No. 3,051,750 and No. 3,519,693. It is also taught in U.S. Pat. No. 3,051,750 that such a reaction must be carried out at temperatures in a range of about 0° C. to 10° C. to prevent the evolution of nitrogen oxides which might react with organic reactants to produce undesirable organic by-products. U.S. Pat. No. 2,225,357 discloses that the undesirable nitrogenous fumes can be removed from the reaction chamber by sweeping the atmosphere above the reaction solution with an inert gas.

It is known from U.S. Pat. No. 3,510,527 that nitrous acid, a nitrosating agent, is produced in aqueous nitric acid by addition of specific oxides of nitrogen at a temperature in the range of 0° C. to 10° C. Further, it is taught in this same patent that the nitrous acid can be decomposed to nitric acid and nitric oxide at a temperature in the range of 15° C. to 30° C. and subsequently the nitric oxide can be reformed as nitrous acid in an aqueous solution of nitric acid at a temperature in the range of 0° C. to 10° C.

It is generally desirable to produce a nitrosating agent by a method which does not introduce substantial amounts of alkali metal ions into the nitrosating solution. Repeated recycling of the mother liquor from a nitrosation process employing an alkali metal nitrite produces an excessive concentration of alkali metal ions which create a waste disposal problem complicated by the combination of inorganic ions with the residual organic compounds from the nitrosation. The use of oxides of nitrogen to produce a nitrosating solution does not introduce alkali metal ions into the nitrosating solution. However, the alkali metal nitrite, particularly sodium nitrite, is a less dangerous and a more economical reagent than are any of the oxides of nitrogen.

Nitrosation of a monosubstituted phenylic compound with subsequent oxidation of the nitroso group to a nitrate is a common synthetic method for preparing many disubstituted, para-nitrated phenylic compounds obtained in only low yields from the direct nitration of the related monosubstituted phenylic compounds such as phenol. It is, therefore, desirable to achieve high para-substitution in the nitrosation of monosubstituted phenylic compounds.

It is an object of this invention to prepare from relatively inexpensive reagents a solution of a nitrosating agent substantially free of alkali metal ions.

It is also an object of this invention to segregate in an inorganic solution exclusive of organic components the alkali metal salts produced from the reaction of the mineral acids and the alkali metal nitrite.

It is a further object of this invention to effect nitrosation of a monosubstituted phenylic compound with an unexpectedly high ratio of para- to ortho-substitution.

SUMMARY OF THE INVENTION

The aforementioned objectives are accomplished by a method of preparing a nitrosating agent in an aqueous solution comprising the sequential steps of bringing together an alkali metal nitrite with a strong mineral acid in a first organic or aqueous medium at a temperature in the range from about $-15°$ C. to about 35° C.; generating oxides of nitrogen in said first medium by maintaining or elevating the temperature of the medium to a range from about 15° C. to about 35° C. during or following the bringing together of said nitrite and acid, said oxides evolving into the atmosphere above the medium; and removing said evolved oxides of nitrogen to a second acidic, aqueous solution maintained at a temperature in the range from about $-15°$ C. to about 10° C. to produce the nitrosating agent in said solution.

Surprisingly, the practice of the present invention produces in the second aqueous solution a solution free of alkali metal salts, which is effective in nitrosating aromatic compounds in nuclear positions and produces only a low percentage of products from undesirable side reactions. The reaction of the alkali metal nitrite and mineral acid in a solution separate from the nitrosating solution encourages the use of efficient, but relatively high concentrations of the acid and nitrite, which would inhibit nitrosation in the same solution. Reaction of the nitrite and acid in the first medium, when taken to substantial exhaustion of both reactants, produces a neutral waste stream of an alkali metal salt of the acid which is free of organic contaminants. This waste stream can be readily disposed of or recycled for other uses. The prior art practice of nitrosation of an aromatic compound utilizing alkali metal nitrites produces a mixture of organic and inorganic waste, which limits the number of times the mother liquor can be recycled and is difficult to dispose of in a manner not hazardous to human health or the environment. The prior art practice of nitrosation of an aromatic compound by means of an oxide of nitrogen requires the use of expensive reagents and necessitates more than minimal handling of dangerous oxides of nitrogen.

The method of the present invention possesses great utility in the synthesis of many nitrosated or nitrated phenylic compounds. On especially preferred embodiment of this invention wherein great utility is achieved is the nitrosation of phenolic compounds. For instance, p-nitrosophenol produced from phenol by the method of this invention can be oxidized to form p-nitrophenol which is a valuable chemical intermediate for other chemical compounds useful as insecticides, pharmaceuticals, dyestuffs and antioxidants. p-Nitrosophenol is particularly useful as an intermediate in the synthesis of p-aminophenol and phenylene diamines which have a variety of commercial uses.

DETAILED DESCRIPTION OF THE EMBODIMENTS

The method of bringing together the strong mineral acid with the alkali metal nitrite in the first medium is not critical to the generation of oxides of nitrogen in the practice of this invention. The absolute and the relative concentrations of said acid and said nitrite can suitably vary over wide ranges as the acid-base reaction occurs quickly to the substantial exhaustion of the less concentrated reactant. Preferably, the acid and nitrite are brought together so that concentrations in the ranges from 3.0 to 7.3 molar and 6.0 to 12.3 molar respectively would be effected if the reaction did not occur simultaneous with the bringing together. The preferred molecular ratio of the acid and nitrite is in the range from about 1:1 to 5:2. It is then suitable in the practice of this invention to add the nitrite to an acidic medium, to add said acid to a medium containing said nitrite, or to add said acid and said nitrite to the medium contemporaneously.

The medium in which the alkali metal nitrite and the strong mineral acid are brought together can be organic or aqueous in nature. Generally, organic compounds which are substantially inert to said nitrite, said acid and the oxides of nitrogen are suitable media. Such suitable organic compounds include benzene and perchloroethylene. Generally, the nitrite and the acid are not soluble in organic compounds and an organic medium should be continuously stirred to maintain a slurry in which the acid and the nitrite readily react. Preferably, the alkali metal nitrite and the strong mineral acid are brought together in an aqueous medium.

In general, the alkali metal nitrites suitable for use in the practice of the method of this invention are lithium nitrite, potassium nitrite, and sodium nitrite. Preferably, a single alkali metal nitrite is employed, but a mixture of such nitrites is also suitable. The preferred alkali metal nitrite is sodium nitrite.

The strong mineral acids suitable for use in this invention include sulfuric acid, hydrochloric acid, phosphoric acid, and nitric acid. Of the foregoing suitable acids, nitric acid is less preferred because of the risk of undesirable side reactions with the alkali metal nitrite. Preferably, a single mineral acid is employed, but a mixture of such acids is also suitable. The preferred strong mineral acids are hydrochloric acid and sulfuric acid.

The rate at which the acid and the nitrite are brought together in the medium is preferably slow enough to avoid localized heating in the medium from the exothermic reaction of said acid and nitrite which might create localized regions in the medium with temperatures exceeding the desired range. The acid and nitrite can also suitably be brought together more quickly at temperatures low enough to minimize the undesirable localized heating, preferably about $-15°$ C. Agitation or mixing of the reaction mixture is advantageous to minimize such localized heating. It is suitable in the practice of the method of this invention to add concentrated mineral acid or undissolved alkali metal nitrite to a reaction medium containing the other reactant. Preferably, dilute aqueous solutions of said acid or said nitrite are added dropwise to an aqueous reaction medium containing the other reactant to minimize localized heating effects. More preferably, it is the dilute nitrite solution which is added dropwise.

It is suitable in the practice of this invention to bring together in a medium the alkali metal nitrite and strong mineral acid at a temperature in the range of about $-15°$ C. to about 35° C. The temperature at which said nitrite and acid are initially brought together can be lower than about $-15°$ C., but these low temperatures are not economically desirable. Temperatures in the range of from about 15° C. to 35° C. are preferred, because in this temperature range spontaneous evolution of the oxides of nitrogen occurs substantially simultaneously with the reaction of the nitrite and the acid. The most preferred temperature range is from about 23° C. to about 25° C. The spontaneous evolution of the oxides of nitrogen is desirable because the rate of evolution of the oxides of nitrogen may be easily controlled by the rate at which the reactants are brought together. When the acid and the nitrite are brought together at a temperature less than about 15° C., the temperature of the aqueous medium must be elevated with care to a temperature in the range from about 15° C. to about 35° C. so as to generate the desired oxides of nitrogen. It is convenient in the practice of this invention to bring together the alkali metal nitrite and the strong mineral acid in a medium at a rate whereby the exothermic reaction of said acid and nitrite effects and maintains a solution temperature in the desired range.

The oxides of nitrogen generated in the practice of this invention may vary as to both species and relative concentration depending on the particular reaction conditions employed in the reaction of the nitrite and the acid. The evolved oxides of nitrogen are believed to include, but this invention is not limited to, nitrous oxide, $N_2O$, nitrogen dioxide, $NO_2$, nitrogen trioxide, $N_2O_3$, and dinitrogen tetroxide, $N_2O_4$. Where the strong mineral acid is hydrochloric acid the "oxides of nitrogen", as the term is used in this invention, can also include nitrosyl chloride, $NOCl$.

The atmospheric pressure above the medium wherein the acid and the nitrite react is advantageously not so great as to substantially impede the evolution of the oxides of nitrogen. The pressure above the medium is otherwise not critical. The atmospheric pressure is conveniently in the range from 1 to 2 atmospheres. The atmosphere above the medium preferably consists essentially of a gas inert to oxides of nitrogen, such as nitrogen. The atmosphere can also suitably comprise small amounts of components which react with the oxides of nitrogen, but do not react in the amount present in a manner which will adversely affect the composition of the nitrosating solution prepared by the practice of the method of this invention. Such suitable reactive components include water and oxygen.

The evolved oxides of nitrogen can suitably be stored as a gaseous atmosphere at a temperature in the range from about 15° C. to 35° C. for a brief period. Because of the hazardous nature of the oxides of nitrogen, said oxides are advantageously generated only as needed and are then almost immediately removed by suitable means to a second aqueous solution comprising an acid or acids and which is maintained at a temperature in the range from about $-15°$ C. to about 10° C., preferably in the range from about $-5°$ C. to about 5° C. conveniently, an inert gas stream can be employed to sweep said oxides into solution. It is desirable that the inert gas stream has a flow rate great enough to avoid the excessive atmospheric residence times which occur at too low a flow rate and low enough to promote efficient entry of the oxides of nitrogen into solution. The relative desirability of flow rates is advantageously determined empirically, as it depends on such diverse factors as the volume of the reaction medium and the method by which oxides of nitrogen are introduced. The inert gas stream is conveniently maintained at the same temperature and comprises the same composition as that of the atmosphere above both the oxide evolving and the nitrosating solutions. The oxides of nitrogen are readily dissolved in the second aqueous solution can be conveniently sparged, bubbled through or otherwise introduced into the second aqueous solution.

It is believed, but the scope of this invention is not limited thereby, that the oxides of nitrogen readily undergo hydration in the acidic, aqueous medium to produce predominantly nitrous acid as the nitrosating agent. The acid present in the aqueous medium, during addition of the oxides of nitrogen facilitates hydration of said oxides. Suitable acids include hydrochloric acid, sulfuric acid, nitric acid, and mixtures of the aforementioned strong mineral acids. Carboxylic acids such as formic, acetic, propionic, chloroacetic, hydroxyacetic and oxalic acids are also suitable, but less preferred than the mineral acids. Acetic acid is the carboxylic acid of choice. The preferred acid is sulfuric acid or mixtures of sulfuric acid with nitric acid. Total acid concentrations prior to the addition of the oxides of nitrogen in the range from about 1 to about 10 moles acid per liter of solution are preferred, from about 1 to about 5 moles acid per liter being more preferred, to provide substantially complete and rapid hydration of the oxides of nitrogen. Lower concentrations are suitable so long as the desired degree of hydration occurs. It is also suitable to add an additional amount of acid during nitrosation of the aromatic compound. Conveniently, this additional acid can be added in solution with the aromatic compound.

For the purposes of this invention the nitrosated product need not be isolated, but may be spontaneously oxidized in situ to the corresponding nitrated compound when nitric acid is present in the nitrosating medium. This two-step method of nitration is desirable to effect nitrate substitution at sites on the aromatic compound where direct nitration of the compound may occur in only low yield. To effect the contemporaneous oxidation of the nitroso group to the nitrate it is preferable to have a nitric acid concentration in the range from about 1.2 to about 3.4 moles per liter of the nitrosating solution. Higher concentrations of nitric acid should be avoided to prevent the occurrence of direct nitration of the aromatic compound in preference to nitrosation and subsequent oxidation to the nitrate, but both higher and lower concentrations of nitric acid are suitable, so long as nitrosation occurs in preference to direct nitration and in good yield.

The nitrosating solution prepared as described above is suitable for use in nitrosating nitrosatable aromatic compounds in nuclear positions. Generally, nitrosatable aromatic compounds are those aromatic compounds having one or more exchangeable hydrogen moieties in a nuclear position at which site a nitroso group may be substituted. Preferred compounds include nitrosatable arylbenzenes, alkylbenzenes, phenylamines, and phenols. Toluene, phenol, o-cresol, and m-cresol are even more preferred nitrosatable aromatic compounds. The nitroso substituent generally is introduced at sites occupied by an exchangeable hydrogen predominantly ortho or para relative to the most electron-donating substituent. Where the nitrosatable aromatic compound is toluene, phenol, o-cresol or m-cresol, the compound is predominantly nitrosated in a position para relative to the hydroxyl substituent, if there is such a substituent, or para relative to the methyl substituent if there is no hydroxyl substituent.

The composition of the nitrosating solution prepared is not critical to this invention. The prior art discloses a number of nitrosation or nitration processes which could advantageously employ the nitrosating solution prepared by the method of this invention and as modified by the teachings of the prior art. Exemplary references include U.S. Pat. Nos. 3,051,750, 3,320,324, 3,770,834, 3,510,527, and 3,668,261. The nitrosating solution prepared by the method of this invention can then comprise such other components in such concentrations as the prior art discloses may be advantageously employed. It is preferred, however, that the nitrosating solution remains substantially free of alkali metal ions, so that the mother liquor can be conveniently recycled or used in a continuous process. Furthermore, waste handling is simplified by the elimination of such alkali metal ions from the nitrosating solution.

The preferred concentration of the nitrosating agent formed in situ from the oxides of nitrogen is dependent on the degree of nitrosation desired. To effect monoitrosation of a nitrosatable aromatic compound possessing more than one exchangeable hydrogen moiety, a concentration of unreacted nitrosating agent from about 0.1 to about 2 moles per liter of the nitrosating solution is suitable, from about 0.1 to about 0.5 mole per liter of the nitrosating solution being preferred. It is also advantageous to maintain a molecular ratio of the nitrosating agent and nitrosatable aromatic material in the range from 1:10 to 3:2, preferably from 1:1 to 5:8, to effect mononitrosation. Higher concentrations of nitrous acid and higher ratios of the nitrous acid relative to the nitrosatable aromatic compond are desirable to effect dinitrosation or an even higher degree of nitrosation. A concentration of nitrous acid less than about 0.05 mole per liter is generally not desirable when nitric acid is present as direct nitration of the aromatic compound is likely to predominate over the desired nitrosation.

The rate and conditions at which the nitrosating agent and nitrosatable aromatic compound are brought together in the aqueous reaction medium can significantly effect the yield of nitrosated compounds and presence of undesirable products of side reactions. It is suitable in nitrosating the aromatic compound to add said compound to the acidic, aqueous medium before the oxides of nitrogen are swept into the solution in accordance with the method of this invention. However, if nitric acid is present in the reaction medium direct nitration can predominate over nitrosation. It is preferred to begin the addition of the oxides of nitrogen to the acidic, aqueous medium slightly before or substantially simultaneous with the addition of the nitrosatable aromatic compound to the solution. A concentration of nitrous acid and a ratio of nitrous acid and aromatic compound in the aforementioned preferred ranges can be quickly attained during addition and are preferably maintained substantially continuously to substantial completion of the nitrosation. Conveniently, the nitrosation can be effected continuously and the nitrosated or nitrated product simultaneously removed in any well-known manner as by filtering or centrifuging.

The nitrosatable aromatic compound is advantageously added to the nitrosating solution dropwise from a dilute solution of the aromatic compound. The solvent in the dilute solution can be water or a water-miscible, preferably inert solvent, such as acetic acid or the like. Generally, the nitrosation of the aromatic compound is an exothermic reaction and the addition from a dilute solution helps to minimize localized regions of high temperature in the solution. Mixing or agitation of the nitrosating solution is desirable to avoid such "hot spots" and to promote uniform nitrosation. The nitrosating solution is suitably maintained at a temperature in the range from about −20° C. to about +25° C., preferably from about −15° C. to about +20° C., more preferably from about −15° C. to about +10° C., during nitrosation of the aromatic compound. Cooling is necessary to maintain the desired temperature and is conveniently achieved by cooling coils or circulating cooling medium through the reaction vessel jacket.

Typically, the time required for substantially complete nitrosation, i.e., the period of time from when the aromatic compound and nitrosating agent are completely brought together to when one of the reactants is substantially exhausted, is from about 1.5 to 3 hours.

A particularly useful embodiment of this invention involves the mononitration of phenol in a predominantly para position. In this embodiment, oxides of nitrogen, generated by the reaction of sodium nitrite and hydrochloric acid in an aqueous solution at a temperature in the range from 23° C. to 25° C., are swept by a nitrogen gas stream into a second acidic, aqueous medium maintained at a temperature in the range from about −10° C. to 0° C. The acid in the second aqueous medium comprises a mixture of from 1.7 to 3 molar sulfuric acid and from 1.2 to 3 molar nitric acid. The oxides of nitrogen are swept over into the second aqueous medium so as to produce an initial concentration of the nitrosating agent in the range from about 0.05 to 0.15 molar and the phenol is then added dropwise to the nitrosating solution. A molecular ratio of the nitrosating agent and phenol in the range from about 1:3 to 1:10 is maintained to promote mononitrosation. The predominantly p-nitrosophenol product is oxidized in the presence of nitric acid to p-nitrophenol. In this embodiment, an unexpectedly high ratio of p-nitrophenol relative to the ortho isomer is effected. Ratios of para to ortho as high as 28.5:1 have been achieved in this embodiment of the invention.

PROCEDURE IN EXAMPLES

The specific examples that follow illustrate the invention, but are not to be taken as limiting its scope. Concentrations are stated in moles per liter unless otherwise indicated and in the case of reactants refer to concentrations effected if the material was not reacting during addition.

The apparatus used in the methods embodying this invention consists essentially of two 500-milliliter (ml) reaction flasks joined by a gas line for transferring the oxides of nitrogen. The two flasks are sealed so that the enclosed atmosphere will not be diluted or contaminated. In the first reaction flask, hereafter referred to as Flask I, the alkali metal nitrite reacts with a strong mineral acid in the practice of this invention. Flask I is fitted with a sparging tube connected to a source of nitrogen, an addition flask, a thermometer, and a gas exit tube connected by means of the line for transferring gas to a sparging tube in the second reaction flask, hereafter referred to as Flask II. The nitrosating solution is formed in situ in Flask II. Flask II, in addition to the sparging tube, is fitted with a stirring rod, a thermometer, an addition flask or pump for addition of phenol, and a gas exit tube connected to a gas bubbler tube or a gas reservoir to preserve the integrity of the internal atmosphere.

Unless otherwise indicated, in the methods embodying this invention a solution of sodium nitrite is added dropwise to a solution of hydrochloric acid in Flask I maintained at a temperature in the range of 23° C.–25° C. during the addition. Nitrogen is continuously sparged through the solution in Flask I during addition of the sodium nitrite, thus sweeping the evolved oxides of nitrogen into Flask II. The desired temperature range in Flask I is maintained by external cooling of the flask, adjusting the drop rate of the sodium nitrite and intermittently stopping the addition entirely.

The solution in Flask II comprises an acid or mixture of acids at a temperature maintained below about 0° C. substantially to completion of the nitrosation reaction. Phenol, the aromatic compound nitrosated, is generally added dropwise to the nitrosating solution in Flask II with continuous stirring over a period of about one-half to three hours with the addition beginning simultaneously with or 5 to 10 minutes after the evolution of oxides of nitrogen has begun. In some instances all of the phenol is present in the solution in Flask II when the oxides of nitrogen are sparged into the solution.

The nitrosation in Flask II is continued with stirring for a period of 1 to 2½ hours after addition of the phenol. In the instances in which the nitrosophenol product is oxidized with nitric acid to the nitrophenol in situ, the temperature of the solution in Flask II was raised to 30° C. after addition of the phenol.

The product is collected at 0° C. as a precipitate on a filter. The filtrate was then washed with ice water and dried in vacuo.

EXAMPLE 1

Methods 1 and 2 in this example are embodiments of the invention claimed. In Method 1 the phenol is present in the solution in Flask II when the oxides of nitrogen are sparged into the solution. In Method 2 the phenol is added dropwise to the solution in Flask II contemporaneously with the addition of nitrites to the solution in Flask I. Where indicated the phenol solution comprises some acetic acid. The procedure under the two methods is otherwise substantially identical and conforms to that set out in the procedure section above.

Under Methods 1 and 2 the acid in the solution in Flask II prior to sparging with the oxides of nitrogen consists essentially of acetic acid. The concentrations by weight percent of the sodium nitrite solution and the hydrochloric acid solution in Flask I to which said nitrite solution is added are before addition 31 percent and 37.8 percent, respectively, in each of the nitrosations consistent with these two methods. The concentration of the acetic acid in the aqueous solution in Flask II is either 12.4 moles per liter or 14.5 moles per liter for the nitrosations pursuant to Methods 1 and 2. In the second and third of the three nitrosations in accord with Method 2, 0.05 and 0.03 mole, respectively, of acetic acid is present in the phenol solutions to be added to the aqueous acetic acid solution in Flask II. The product after nitrosation is collected as a solid, dried in vacuo, and the yield of nitrosophenol determined by iodide-thiosulfate titration.

Method 3 is identical to Method 1 except that nitrogen trioxide was added to the aqueous hydrochloric acid solution in place of sodium nitrite. The molarity of the acetic acid was 14.5 in this nitrosation. This method, while apparently not anticipated in the art, is not claimed as an embodiment of this invention because this use of nitrogen trioxide is similar to prior art uses as illustrated by U.S. Pat. No. 3,770,834. In contrast, the claimed method of preparing a nitrosation solution is more economical, eliminates the handling of oxides of nitrogen until required for nitrosation and possesses unexpected efficiency in nitrosation.

Method 4 is consistent with the prior art methods of nitrosation such as that disclosed in the example in U.S. Pat. No. 3,770,834, wherein the aromatic compound to be nitrosated is treated with nitrogen trioxide in an aqueous solution comprising strong acids. The phenol in this instance is added dropwise simultaneously with the nitrogen trioxide to a solution of 0.75 molar sulfuric acid at 0° C. The reaction mixture is stirred for ninety minutes after the completion of addition. The product is collected as a solid, dried in vacuo, and once again the yield of nitrosophenol determined.

The moles of reactants, temperature, times, and yield of nitrosophenol for each of the experimental runs for the aforementioned methods are recorded in Table I.

It is evident from the data presented in Table I that nitrosation by Methods 1 and 2 does not effect as great a yield of nitrosated product as does the prior art practice exemplified in Method 4. The greater yield of nitrosophenol from the practice of Method 4 is attributable to the presence in the nitrosating solution of sulfuric acid in place of the weaker acetic acid present in Methods 1–3.

is added dropwise to the solution in Flask II substantially contemporaneous with the sparging of the solution with the oxides of nitrogen. The addition of phenol is initiated simultaneous with or a few minutes after the oxides of nitrogen begin to evolve and is stopped intermittently so as to prevent the temperature of Flask II from exceeding the desired range. The evolution of nitrogen oxides is independently halted or slowed intermittently by the cessation of the addition of sodium nitrite to Flask I so as to maintain the desired temperature range.

In Method 1 sodium nitrite solution is added to the aqueous solution of hydrochloric acid in Flask I substantially all at one time at a temperature of about 23° C. The temperature of the solution in Flask II when the oxides of nitrogen are sparged into it is about 0° C. in the first three nitrations by this method and is about −15° C. in the fourth of these nitrations.

TABLE I

| Method of Nitrosation | NaNO$_2$ (moles) | HCl (moles) | Acetic Acid (moles) | Phenol (moles) | Temperature (°C.) | Addition Time (minutes) | Post-Addition Time (minutes) | Yield Nitrosophenol (% theoretical yield) |
|---|---|---|---|---|---|---|---|---|
| 1 | 0.13 | 0.31 | 0.87 | 0.1 | −1 to +9 | 45 | 60 | 42.2 |
| 1 | 0.26 | 0.31 | 0.87 | 0.2 | −3 to −8 | 85 | 80 | 41.0 |
| 2 | 0.26 | 0.31 | 0.87 | 0.2 | −3 to −7 | 65 | 155 | 34.0 |
| 2 | 0.26 | 0.37 | 0.92*** | 0.2 | −4 to −8 | 170 | 80 | 51.5 |
| 2 | 0.26 | 0.37 | 1.77*** | 0.2 | −2 to −7 | 165 | 75 | 32.7 |
| 3* | 0.06** | 0.31 | 0.87 | 0.05 | −2 to +3 | 30 | 60 | 40.8 |
| 4* | 0.46** | — | 0.75** | 1.0 | 0 to −3 | 120 | 90 | 80.5 |

*Not an example of this invention.
**Substitution for listed reactant; N$_2$O$_3$ used in place of NaNO$_2$ or sulfuric acid for acetic acid.
***Included in the total acetic acid is 2 to 3 ml added with the phenol solution.

The yield of nitrosophenol by Method 3, where an acidic, aqueous solution comprising nitrogen trioxide is utilized to reform nitrous acid for nitrosation in a manner otherwise identical to Method 1, is substantially equal to the yield obtained by Method 1 and falls within the range of yields obtained by Method 2. Furthermore, it is possible to repeatedly recycle the mother liquor from Methods 1, 2 and 3, thus nitrosating the residual amounts of phenol in the mother liquor, so as to effect higher total yields of nitrosophenol.

It is evident in comparison of the embodiments of Methods 1 and 2 of this example that the compound to be nitrosated may be added incrementally to the nitrosating solution or added all at once prior to the initiation of nitrosation in the practice of this invention.

EXAMPLE 2

Methods 1–6 in this example are embodiments of the invention in which the nitrosophenol is oxidized in situ to nitrophenol. The procedure in Methods 1–6 is consistent with that set out in the procedure section above with the additions and differences noted hereinafter. The concentrations by weight of the hydrochloric acid solution in Flask I and the sodium nitrite solution before addition are 37.8 percent and 31 percent, respectively, in Methods 1–6. In all the nitrations pursuant to Methods 1–6 the concentration of nitric acid in Flask II is in the range from 1.2 to 3.0 moles per liter. In the nitrations in accord with Methods 1–4 and in accord with Method 5 the solution in Flask II comprises sulfuric acid and hydrochloric acid, respectively; in each instance the acids possess a concentration in the range from 1.7 to 2.9 moles per liter. In Method 6 only nitric acid is present in the solution in Flask II. In all the methods embodying the invention, the phenol solution In Methods 2–6 the sodium nitrite solution is added dropwise to the acid solution in Flask I. Methods 2, 3 and 4 are substantially identical in practice with the exception of the rate of nitrogen flow through the gas transfer line during evolution of the oxides of nitrogen, which is 250, 75 and 125 ml per minute, respectively.

Methods 4, 5 and 6 are all substantially the same with the exception of the acids comprised in the aqueous solution in Flask II. The practice of Method 4 requires both nitric and sulfuric acid, whereas Method 5 requires both nitric and hydrochloric acid and Method 6 calls for only nitric acid. The nitrogen flow rate in the practice of all three methods is 125 ml per minute.

Method 7 is an embodiment of the prior art practice of direct nitration of phenol with nitric acid. No acid or sodium nitrite is present in Flask I, but a 125 ml per minute nitrogen flow is utilized to minimize the differences between this method and those which embody this invention. The phenol is added dropwise to a solution of sulfuric and nitric acid in Flask II.

Method 8 is an embodiment of the prior art practice of nitrosation of phenol with sodium nitrite in an acidic, aqueous solution and oxidation of the product in situ with nitric acid. This practice is illustrated by Example 16 of U.S. Pat. No. 3,519,693. The phenol is added dropwise to a solution of 1.8 moles sulfuric acid per liter, 1.3 moles nitric acid per liter and 0.6 mole sodium nitrite per liter.

The crude product recovered by precipitation in the practice of each of the foregoing methods is dried in vacuo and weighed. The yield is determined as a percentage of the yield theoretically possible if all of the sodium nitrite had been converted to a nitrosating agent and a nitrated product recovered in 100 percent yield based on the phenol present.

For the product recovered from the practice of Methods 1, 2 and 3, the relative ratios of o- and p-nitrophenol in the crude product are roughly determined from peak area ratios in gas phase chromatography without internal standards in a manner well-known in the art. In Methods 4–8 the relative ratios of p- and o-nitrophenol in the crude product are determined by gas phase chromatography with internal standards. The number of moles of the reactants, crude yield of the product, and relative ratios of o- and p-nitrophenol are tabulated in Table II for each of the nitrations.

By employing the method of preparing a nitrosating solution taught in this invention, high yields of nitrophenol can be effected with unexpectedly high ratios of para-substituted to ortho-substituted product. The failure of the nitrations employing Methods 1–3 to effect consistently high measured yields and ratios can be attributed to a number of factors.

TABLE II

| Method of Nitrosation | Flask I | | Flask II | | | | Addition Time (minutes) | Crude Yield (% theoretical yield) | Ratio of para/ortho |
|---|---|---|---|---|---|---|---|---|---|
| | NaNO$_2$ (moles) | HCl (moles) | H$_2$SO$_4$ (moles) | HNO$_3$ (moles) | Phenol (moles) | Temperature (°C.) | | | |
| 1 | 0.136 | 0.37 | 0.455 | 0.327 | 0.207 | −5.5 to −1.5 | 120 | 66.9 | 3.7 |
| 1 | 0.136 | 0.37 | 0.455 | 0.327 | 0.207 | −3.5 to −1.5 | 120 | 62.7 | 3.1 |
| 1 | 0.136 | 0.37 | 0.455 | 0.327 | 0.207 | −5.0 to −1.5 | 150 | 65.1 | 4.8 |
| 1 | 0.136 | 0.37 | 0.455 | 0.327 | 0.207 | −4.0 to −1.0 | 150 | 55.5 | 21.6 |
| 2 | 0.204 | 0.37 | 0.683 | 0.490 | 0.260 | −4.5 to −1.0 | 140 | 86.6 | 2.9 |
| 2 | 0.204 | 0.55 | 0.683 | 0.490 | 0.260 | −8.0 to −2.0 | 143 | 77.5 | 8.2 |
| 3 | 0.204 | 0.55 | 0.683 | 0.490 | 0.260 | −9.0 to −2.0 | 153 | 82.4 | 5.3 |
| 4 | 0.204 | 0.55 | 0.683 | 0.490 | 0.260 | −8.0 to −1.5 | 141 | 90.1 | 21.6 |
| 4 | 0.204 | 0.22 | 0.683 | 0.490 | 0.260 | −7.0 to −1.0 | 147 | 82.5 | 8.3 |
| 4 | 0.248 | 0.66 | 0.800 | 0.589 | 0.313 | −8.5 to −1.0 | 150 | 92.0 | 9.9 |
| 4 | 0.220 | 0.69 | 0.587 | 0.790 | 0.250 | −8.0 to −3.0 | 225 | 87.1 | 19.0 |
| 4 | 0.408 | 0.91 | 1.366 | 0.980 | 0.500 | −8.0 to −5.0 | 150 | 77.1 | 28.5 |
| 5 | 0.220 | 0.69 | 0.584** | 0.790 | 0.250 | −9.0 to −1.5 | 150 | 82.3 | 8.6 |
| 5 | 0.240 | 0.69 | 0.642** | 0.868 | 0.275 | −9.0 to −1.0 | 175 | ? | 9.9 |
| 6 | 0.220 | 0.69 | 0 | 0.790 | 0.250 | −8.0 to −1.0 | 150 | 60.4 | 18.0 |
| 7* | 0 | 0 | 0.580 | 0.790 | 0.500 | −7.0 to −0 | 150 | 59.9 | 4.1 |
| 7* | 0 | 0 | 1.366 | 0.980 | 0.500 | −7.0 to −3.0 | 225 | 75.9 | 4.7 |
| 8* | 0.140 | 0 | 0.450 | 0.330 | 0.210 | −3.5 to −1.0 | 120 | 85.6 | 11.5 |

*Not an example of this invention; only a single reaction vessel is used.
**HCl acid substituted for the listed H$_2$SO$_4$.

The flow rate of nitrogen in these nitrations are in the spurious cases too high to effect efficient transfer of the oxides of nitrogen to the solution or too low to achieve the concentration of nitrosating agent necessary to prevent direct nitration. The low ratios of p-nitrophenol relative to o-nitrophenol reported in Methods 1–3 can be attributed to the manner in which the oxides of nitrogen are introduced into Flask II. In the first three runs in Method 1 the temperature of the medium in Flask II is too high to efficiently absorb the uncontrolled evolution of the oxides of nitrogen which occurs when the nitrite is added all at once to Flask I. In Methods 2 and 3 the rate of nitrogen flow in the gas transfer line is too high in the former method and too low in the latter to effectively form the nitrosating agent in Flask II quickly enough to reduce direct nitration.

A comparison of the nitrations pursuant to Method 4 with the nitrations known in the prior art, as illustrated in Methods 7 and 8, demonstrates the value of the claimed method of preparing a nitrosating solution. The high yield of p-nitrophenol and favorable ratio of the para to ortho isomer indicates that Method 4 possesses great synthetic utility. In contrast, the use of solutions in Flask II comprising hydrochloric and nitric acids or nitric acid alone, as in Methods 5 and 6, respectively, are less preferred because the former produces a lower ratio of p-nitrophenol and the latter produces a lower yield of product.

What is claimed is:

1. A method of preparing a nitrosating agent in an aqueous solution comprising the sequential steps of:
    (a) bringing together an alkali metal nitrite with a strong mineral acid in a first aqueous medium at a temperature in the range from about −15° C. to about 35° C.;
    (b) generating oxides of nitrogen in said first medium by maintaining or elevating the temperature of the medium to a range from about 15° C. to about 35° C. during or following the bringing together of said nitrite and acid, said oxides evolving into the atmosphere above the medium; and
    (c) removing said evolved oxides of nitrogen to a second acidic, aqueous solution, comprising an acid or mixture of acids selected from the group consisting of nitric acid, hydrochloric acid, sulfuric acid and acetic acid, maintained at a temperature in the range from about −15° C. to about 10° C. to produce the nitrosating agent in said solution.

2. The method as defined in claim 1 wherein the second acidic, aqueous solution is substantially free of alkali metal ions and comprises an acid or mixture of acids selected from the group consisting of nitric acid, hydrochloric acid and sulfuric acid, said solution having a total concentration of acid in the range from about 1 to about 10 total moles of acid per liter of solution.

3. The method as defined in claim 1 wherein the second acidic, aqueous solution is substantially free of alkali metal ions and consists essentially of acetic acid in an aqueous solution.

4. The method as defined in claim 2 wherein the first medium is maintained at a temperature in the range from about 15° C. to about 35° C. while bringing together the alkali metal nitrite and strong mineral acid, so that oxides of nitrogen are generated spontaneously by the reaction of said acid and said nitrite.

5. The method as defined in claim 4 wherein the alkali metal nitrite is first dissolved in an aqueous medium and is then added dropwise to the first medium which comprises an aqueous solution of hydrochloric acid or sulfuric acid.

6. The method as defined in claim 5 wherein the alkali metal nitrite is sodium nitrite, the acid in the first aqueous solution consists essentially of hydrochloric acid, and the acid in the second acidic, aqueous solution consists essentially of sulfuric acid or a mixture of sulfuric and nitric acids, having a total acid concentration in the range from about 1 to about 5 moles total acid per liter.

7. The method as defined in claim 6 wherein the sodium nitrite and hydrochloric acid are reacted at a temperature in the range from about 23° C. to 25° C.

8. A method of nitrosating a phenylic compound nitrosatable in a nuclear position with a nitrosating agent in solution comprising the sequential steps of:
 (a) bringing together an alkali metal nitrite with a strong mineral acid in a first aqueous medium at a temperature in the range from about −15° C. to about 35° C.;
 (b) generating oxides of nitrogen in said first medium by maintaining or elevating the temperature of the medium to a range from about 15° C. to about 35° C., said oxides evolving into the atmosphere above the medium;
 (c) removing said evolved oxides of nitrogen into a second acidic, aqueous solution maintained at a temperature in the range from about −15° C. to about 10° C.; and
 (d) bringing together said nitrosatable phenylic compound with said evolved oxides of nitrogen in the seond acidic, aqueous solution, comprising an acid or mixture of acids selected from the group consisting of nitric acid, hydrochloric acid, sulfuric acid and acetic acid, at a temperature in the range of from about −20° C. to about 25° C.

9. The method as defined in claim 8 wherein the nitrosatable compound is selected from the group consisting of toluene, phenol, o-cresol and m-cresol.

10. The method as defined in claim 8 wherein the second acidic, aqueous solution is Step (c) is substantially free of alkali metal ions and comprises an acid or mixture of acids selected from the group consisting of nitric acid, hydrochloric acid, sulfuric acid, and mixtures thereof having a total concentration of acid in the range of from about 1 to about 10 total moles of acid per liter of solution.

11. The method as defined in claim 8 wherein the oxides of nitrogen and nitrosatable phenylic compounds are brought together so as to substantially continuously effect during the nitrosation a concentration of the nitrosating agent in the range from about 0.1 to about 0.5 mole per liter of solution and so as to effect a ratio of the nitrosating agent to said phenylic compound in the range from 1:1 to 5:8.

12. The method as defined in claim 11 wherein the nitrosatable phenylic compound is phenol, and the resulting nitrosated compound is predominantly p-nitrosophenol.

13. In the nitrosation of a nitrosatable phenylic compound with a nitrosating agent prepared by the addition of oxides of nitrogen to an aqueous solution comprising an acid or mixture of acids selected from the group consisting of nitric acid, hydrochloric acid and sulfuric acid at reactive conditions, the improvement wherein the oxides of nitrogen are generated at a temperature in the range from about 15° C. to about 35° C. from a separate solution in which an alkali metal nitrite is brought together with a strong mineral acid.

14. The method as defined in claim 11 wherein the nitrosatable compound is selected from the group consisting of phenol, o-cresol and m-cresol.

* * * * *

UNITED STATES PATENT AND TRADEMARK OFFICE
CERTIFICATE OF CORRECTION

PATENT NO. : 4,232,175

DATED : November 4, 1980

INVENTOR(S) : William E. Smith and Thomas W. McGee

It is certified that error appears in the above—identified patent and that said Letters Patent is hereby corrected as shown below:

Title and abstract page, column 2, line 12, delete "nitrate" and insert --nitrite--.

Column 2, line 45, delete "On" and insert --One--.

Column 4, line 47, delete "conve-" and insert -- Conve- --.

Column 4, line 62, insert --and-- between "solution" and "can".

Column 6, line 10, delete "monoi-" and insert -- mononi- --.

Column 6, line 22, delete "compond" and insert --compound--.

Column 10, line 12, insert --the-- between "Method 1" and "sodium".

Column 13, line 32, delete "seond" and insert --second--.

Column 14, line 5, delete "is" between "solution" and "Step (c)" and insert --in--.

Column 14, line 10, delete "of" between "range" and "from".

Signed and Sealed this

Twenty-fourth Day of March 1981

[SEAL]

Attest:

RENE D. TEGTMEYER

Attesting Officer

Acting Commissioner of Patents and Trademarks